United States Patent
Stahl et al.

(10) Patent No.: US 6,192,738 B1
(45) Date of Patent: Feb. 27, 2001

(54) METHOD AND ARRANGEMENT FOR ANALYZING EXHAUST GAS FROM AN INTERNAL COMBUSTION ENGINE

(75) Inventors: Roland Stahl, Freiberg; Dietrich Adolph, Albershausen; Gerhard Hoetzel, Stuttgart; Johann Riegel, Bietigheim-Bissingen, all of (DE)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 09/244,933

(22) Filed: Feb. 4, 1999

(30) Foreign Application Priority Data

Feb. 7, 1998 (DE) ............................................ 198 04 985

(51) Int. Cl.$^7$ ...................................................... G01N 7/00
(52) U.S. Cl. ...................... 73/23.32; 73/23.31; 73/117.3; 123/703
(58) Field of Search ............................... 73/23.32, 117.3; 250/339.07; 123/703

(56) References Cited

U.S. PATENT DOCUMENTS

| | | | |
|---|---|---|---|
| 3,593,023 | * 7/1971 | Dodson et al. | 250/43.5 |
| 3,696,247 | * 10/1972 | McIntosh et al. | 250/63.3 H |
| 5,285,676 | * 2/1994 | Adams | 73/23.32 |
| 5,450,749 | * 9/1995 | Strom et al. | 73/117.3 |
| 5,507,174 | * 4/1996 | Friese et al. | 73/23.32 |
| 5,569,847 | * 10/1996 | Hasegawa et al. | 73/117.3 |
| 5,925,088 | * 7/1999 | Nasu | 701/103 |
| 6,055,844 | * 5/2000 | Kondo et al. | 73/23.32 |
| 6,067,841 | * 5/2000 | Suzuki et al. | 73/23.32 |

FOREIGN PATENT DOCUMENTS 2-130460 * 5/1990 (JP) ...................................... 73/23.32

OTHER PUBLICATIONS

Silvis, William M., An Algorithm for Calculating the Air/Fuel Ratio Exhaust Emissions, 1997, SAE 970514, pp. 141–152.*
Jurgen, Ronald K., Automotive electronics handbook, 1995, McGraw–Hill Inc., pp. 6.1–6.23.*
Ueno, Sadayasu, Wide–Range Air–Fuel Ratio Sensor, 1986, SAE 860409, pp. 27–33.*
Simons, Wilhelm, Equations to Determine the Air/Fuel Ratio in S.I. Engines, 1985, p. 257 (abstract and equations only).*

(List continued on next page.)

Primary Examiner—Hezron Williams
Assistant Examiner—Charles D. Garber
(74) Attorney, Agent, or Firm—Michael J. Striker

(57) ABSTRACT

In order to provide a method and arrangement for analytical determination of the relative amounts of exhaust gas components, except for water, but including hydrogen in the rich range or oxygen in the lean range, and for determining a λ value, in which the exhaust gas sample can be taken at any arbitrary location, an arrangement is provided in which at least one portion of the exhaust gas is passed through a catalytic reactor (2, 22), a condenser (3,23) connected to the catalytic reactor to receive the gas passed through it, and, after passing through the condenser, the gas passes through an IR spectrometer and by a λ-sensor. The oxidizable and reducible components of the exhaust gas are reacted with each other in the catalytic reactor which is heated to temperatures greater than 450° C. The relative amounts of $CO_2$, hydrocarbons and, if present, CO are measured with the IR spectrometer and either the relative amount of hydrogen in the rich range or of $O_2+½$ NO in the lean range is determined with the help of the signal ($I_p$) from the λ-sensor. A λ value is calculated from the measured exhaust gas component concentrations or relative amounts.

14 Claims, 2 Drawing Sheets

OTHER PUBLICATIONS

Brettschneider, Von Johannes, Calculation of the Air Ratio of Air–Fuel Mixtures and the Influence of Measurement Error on Lambda, 1979, Bosch Technische Berichte, pp. 177–186 (abstract and equations only).*

"Wide–Range Air–Fuel Ration Sensor", Sadayasu Ueno, Norio Ichikawa, Seiko Suzuki, Kazuyoshi Terakado, SAE Technical Papers DSeries 860409, pp. 27–33.

"Gleichungen Zur Bestimmungen Der Luftzahl Bei Ottomotoren", W. Simons, MTZ Motortechnische Zeitschrift 46 (1985) Jul. 8, 257–259.

"An Algorithm for Calculating the Air/Fuel Ratio From Exhaust Emissions", by W.M.Silvis, pp. 141–152.

"Automotive Electronic Handbook" (1995), McGraw Hill Inc., Kapitel 6, "Exhaust Gas Sensors".

"Berechnung Des Luftverhaeltnisses Von Luft–Kratstoff–Gemischen . . ." by J. Brettschneider, Bosch Technische Berichte 6 (1979) 4, pp. 177–186.

* cited by examiner

METHOD AND ARRANGEMENT FOR ANALYZING EXHAUST GAS FROM AN INTERNAL COMBUSTION ENGINE

BACKGROUND OF THE INVENTION

1. Field of the Invention

The subject matter of the invention concerns an arrangement and method, especially using the arrangement of the invention, for analyzing exhaust gas from an internal combustion engine, in which at least a part of the exhaust gas flows past a λ-sensor and through an IR spectrometer after passing through a condenser connected to the IR spectrometer upstream of the IR spectrometer in an exhaust gas flow direction.

2. Prior Art

The so-called λ value is an important parameter in relation to fuel combustion in internal combustion engines and the ever more stringent requirements for reduction of exhaust gas emission from this type of motor. The λ value is equal to the actual air/fuel ratio divided by the stoichiometric air/fuel ratio. An engine produces less noxious exhaust gases, the closer the λ value is to one. Methods to determine or control the λ value are thus important. Exhaust gas parameters are consulted for determination and/or control purposes.

In the book "Automotive Electronics Handbook", McGraw Hill, Inc., 1995, in Chapter 6, "Exhaust Gas Sensors", sensors are described, which include a sensor (designated in the following as a λ-sensor), which is operated as a combination of a sensor based on the Nernst principle and a diffusion flow probe, which are immersed in the flow of exhaust gas from the internal combustion engine. This λ-sensor is used for control of the λ value of the λ-value-dependent measured flow. A In the paper "Air-Fuel Ratio Sensor for Rich, Stoichiometric and Lean Ranges" of S. Suzuki, among others, published in the SAE Technical Papers Series 860408, pp. 18ff. (reprinted from SP-655 Sensors and Actuators (1986)) a λ-sensor is described, with which it can be established whether the λ value is in the rich, stoichiometric or lean range.

Determination of the λ value from the signal of a λ-sensor is known. The water gas equilibrium is included in the calculation. Since hydrogen and the water vapor concentrations are not measured in the gas phase, the water gas equilibrium is called upon for determination of the λvalue. A value of 3.6 is used for the equilibrium constant $K_p$, but only immediately downstream of the engine. An exhaust gas catalytic converter can greatly change the water gas equilibrium. Current catalytic converters scarcely change the water gas equilibrium of course, but only because sulfur from the fuel blocks these changes. If the fuel does not contain sulfur, the water gas equilibrium changes greatly in the catalytic converter. Thus in this latter case the λ value can only be determined immediately behind or downstream of the engine.

One other method of calculating the λ value is described in the paper of J. Brettschneider, "Calculation of the air ratio of air-fuel mixtures and the influence of measurement errors on λ", in Bosch Technische Berichte (Technical Report), Bd. (Vol) 6, Heft(part) 4 (1979), pp. 177 to 186 and Bosch Technische Berichte (Technical Report), Heft(part) 56 (1994), pp. 30 to 45. In this method CO, $CO_2$ and HC (hydrocarbons in the exhaust gas) are determined by means of an IR spectrometer, for example $O_2$ polarographically or by EPR spectroscopic methods, and, if necessary, No by means of chemiluminescence measurements, since water vapor would be condensed prior to that measurement. When the determination of NO must be avoided because of its expense, some accuracy is lost. Rich exhaust gas and lean exhaust gas having λ values approaching 1 (in the latter case having λ values that lie just above one) contain hydrogen. The water gas equilibrium is included in the calculation. Thus the above-mentioned problems also occur here in the Brettschneider method.

An additional method for calculation of λ has been given by W. Simons, who has determined that an oxygen measurement provides an additional degree of freedom, which can be used in order to calculate the equilibrium constant $K_p$ (see the article "Calculations for determination of the excess air coefficient" in MTZ Motortechnische Zeitschrift (Motor Engineering Journal) 46, 7/8 (1985), pp. 257 to 259). This method thus does not have 'the inherent limitations of the Brettschneider method in regard to the place at which the exhaust gas sample is taken, but is not very accurate.

Finally a method of calculation of λ is described in an article entitled "An Algorithm for Calculating the Air/Fuel Ratio from Exhaust Emissions", by W. M. Silvis, Nr. 970514, Society of Automotive Engineers (1997), pp. 141 to 152. In the described algorithm the water moles are determined either according to the Brettschneider method, in which a value for the equilibrium constant $K_p$ is between 3.5 and 3.8, or according to the Simons method by means of the nitrogen and the mole balance.

SUMMARY OF THE INVENTION

It is an object of the present invention to provide an arrangement and method for determining the relative amounts of the ingredients present in the exhaust gas, except for the relative amount of water, but including the relative amount of hydrogen in rich exhaust gas or the relative amount of oxygen in lean exhaust gas.

It is also an object of the present invention to provide a method for determining λ values, in which the place at which the exhaust gas sample is taken, is arbitrarily selectable, and is independent of the operating conditions in the catalytic converter, such as temperature, spatial velocity, state of the catalytic converter, and sulfur content of the fuel and/or exhaust gas.

These objects and others which will be made more apparent hereinafter are attained in an arrangement according to the invention in which a heated catalytic reactor is connected to the internal combustion engine to receive at least a portion of the exhaust gas from the internal combustion engine; a condenser is connected to the heated catalytic reactor downstream of the catalytic reactor in the exhaust gas flow direction to receive the exhaust gas from the catalytic reactor; an IR spectrometer connected to the condenser downstream of the condenser in the exhaust gas flow direction to receive the exhaust gas from the condenser and a λ-sensor connected downstream of the condenser so that the at least one portion of the exhaust gas passes by the λ-sensor after passing through the condenser. The reducible exhaust gas components are reacted with oxidizable exhaust gas components with the above-described methods in the catalytic reactor which is heated to greater than 450° C. and the relative amounts of the components still present downstream from the catalytic reactor, except for the relative amount of water, i.e. the relative amounts of $CO_2$, hydrocarbons and, if present CO, are measured in a known manner, for example, with an IR spectrometer. The relative amount of $H_2$ in the rich range or $O_2+½NO$ in the lean range is determined from the signal of the λ-sensor taking into account the relative amounts determined by means of the IR spectrometer. In the method according to the invention, which particularly is performed using the arrangement according to the invention, the relative amount of $O_2+½$ NO may be determined more accurately than has currently been possible by means of the λ-sensor and the relative amount of $H_2$ for the first time can be determined and of course with a method that is more economical than previous methods. The unburned hydrocarbon materials are designated with $C_xH_yO_z$ or $C_xH_y$ in the examples.

In a particularly advantageous embodiment of the invention a condenser is also connected upstream of the λ-sensor. With this arrangement in the lean range, since $H_2$ and CO have been removed previously in the heated catalytic reactor and $H_2O$ has been removed in the condenser, the $CO_2$ and HC relative amounts may be determined with the IR spectrometer. The relative amount of $O_2+½$ NO can also be determined by means of the signal $I_p$ from the λ-sensor which satisfies the following equation (I):

$$I_p = K_{O2}[O_2] + K_{NO[NO]-KHC}[HC] \qquad (I)$$

using the hydrocarbon relative amount determined with the IR spectrometer. In the rich range, since $O_2$ and NO have been removed previously in the heated catalytic reactor and $H_2O$ has been removed in the condenser, the $CO_2$, CO and hydrocarbon relative amounts may be determined with the IR spectrometer. Then the relative amount of $H_2$ can be calculated using signal $I_p$ from the λ-sensor that satisfies the following equation (II):

$$I_p = -K_{H2}[H_2] - K_{CO}[CO] - K_{HC}[HC] \qquad (II)$$

using the CO and HC relative amounts determined with the IR spectrometer.

The method according to the invention or an appropriate method is useable in an appropriate manner for determination of the λ value, since the relative amounts of the exhaust gas ingredients determined on the basis of those downstream or behind the condenser is dependent on the λ value. The particular advantage of this method of determination is that practically all required data are obtained by measurement, so that it is not necessary to use parameters of limited applicability that are disclosed in the literature, for example, the constant K for the water gas equilibrium as in the Brettschneider method.

It is advantageous when the λ value in the lean range is determined by the Brettschneider equation, which has a comparatively simple form, and by means of the $H_2$, C, $N_2$ and $O_2$ mass balance between engine intake and outlet of the heated catalytic reactor and also the carbon mass balance between motor intake and measurement apparatus inlet.

Additional advantageous embodiments of the invention are described in the detailed description hereinbelow and claimed in the appended dependent claims.

BRIEF DESCRIPTION OF THE DRAWING

The objects, features and advantages of the invention will now be illustrated in more detail with the aid of the following description of the preferred embodiments, with reference to the accompanying figures in which.

DESCRIPTION OF THE PREFERRED EMBODIMENT

In the following description an example of the arrangement according to the invention and its use in two embodiments of the method according to the invention is described using the example of the combustion of a mixture of air and gasoline of the general formula $C_rH_nO_k$ in an automobile engine. It should be clear that the invention can also be performed with other embodiments of the arrangement according to the invention. The method according to the invention is also suitable for analysis of the combustion in other combustion apparatus, such as diesel motors, using other input fuels, for example those containing no oxygen commonly used in Europe.

Figure 1:
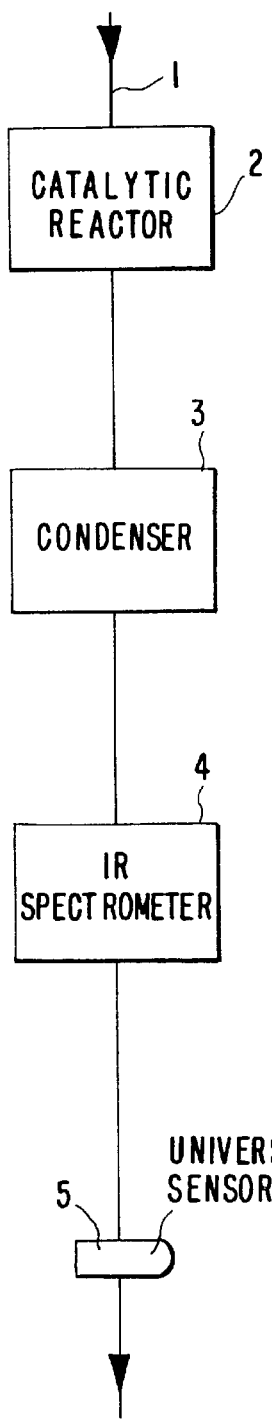
FIG. 1 is a block diagram of one embodiment of an arrangement for analyzing exhaust gas from an internal combustion engine according to the invention.

The arrangement shown in FIG. 1 has an exhaust gas pipe 1, which is connected to the outlet of an automobile engine or an exhaust gas catalytic converter, which is connected downstream from the engine. A heated catalytic reactor 2 is built into the pipe 1. The oxidizable and the reducible species in the exhaust gas react with each other in the catalytic reactor ($O_2$ reacts>200° C. with $H_2$, >230° C. with CO, >400° C. with HC (incompletely), >450° C. with NO). The catalytic reactor 2 provides an environment in which the temperature is greater than 450° C. so that in rich exhaust gas no $O_2$ and no NO appear at its outlet and in lean exhaust gas no $H_2$, no CO but indeed NO (for want of a reaction partner) appear at its outlet. The removal of the water vapor in the condenser 3 occurs downstream in the flow direction of the exhaust gas from the catalytic reactor 2. The exhaust pipe leads to the IR spectrometer 4, in which $CO_2$, HC and, in case it is present, CO are measured. The λ-sensor 5 of this type is built into the exhaust gas pipe 1 downstream from the IR spectrometer so that the exhaust gas passes over or by it.

The λ-sensor 5 is a sensor of a known type, which operates in the lean domain as a diffusion flow sensor and in the rich domain as a boundary flow sensor with opposing flow direction, in which the reversal of the flow direction is performed by an electronic control circuit, which responds to the signal from a Nernst cell contained in the sensor.

Figure 2:
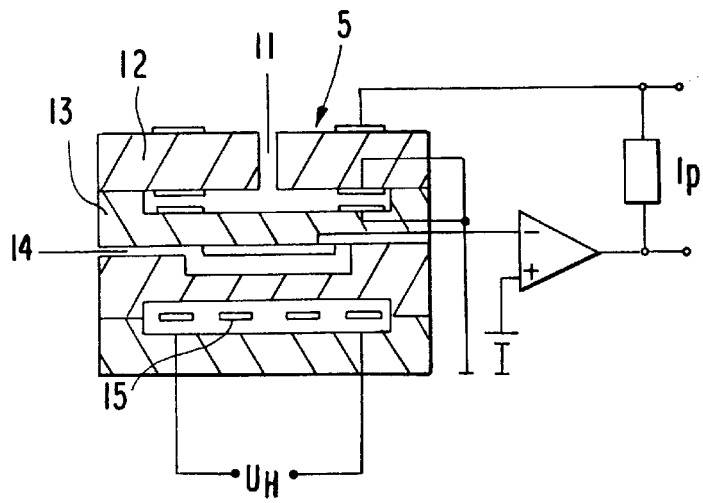
FIG. 2 is a schematic cross-sectional view through on embodiment of a λ-sensor used in the arrangement according to the invention.

FIG. 2 shows a sensor of this type with a diffusion passage 11, the diffusion flow pump cell 12 and the Nernst cell 13, which measures the oxygen partial pressure in the diffusion passage relative to the reference air in the reference gas passage 14. Usually the sensor is controlled at a Nernst voltage of 450 mV in an exhaust gas, which corresponds to the Nernst potential of 450 mV, so that the measured current result is zero. In the lean range a positive measured current is obtained, while in the rich range a negative measured current is obtained. Heating is performed with the heater 15.

Figure 3:
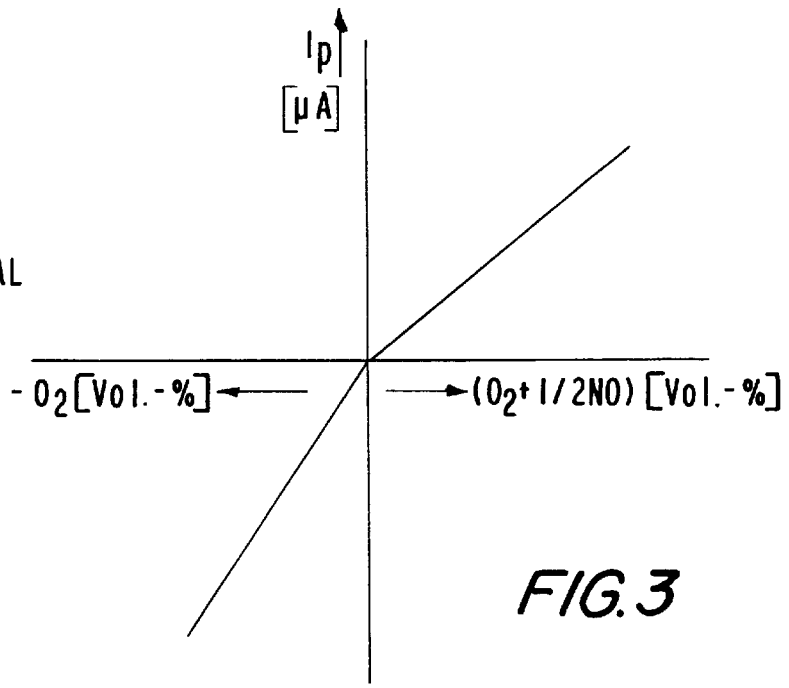
FIG. 3 is a graphical illustration of the sensor signal $I_p$ from the λ-sensor versus the vol. % of $O_2+½$ NO or the $O_2$ deficit in the exhaust gas.

A typical characteristic curve of this type of λ-sensor is shown in FIG. 3. In the positive X-axis branch (lean range) the vol. % content Of $O_2+½$ NO is plotted against the $I_p$ (in μA) and in the negative X-axis branch (rich branch) the oxygen deficit is plotted against the $I_p$. The gases $O_2$, NO, $H_2$, CO and HC are detected by λ-sensors of the above-described type.

In the lean range a smaller relative amount of NO occurs downstream of the heated catalytic reactor than oxygen which is the principle component for the λ-sensor. In the vicinity of λ=1 a small relative amount of $H_2$ from hydrocarbons is not present downstream of the heated catalytic reactor in the lean range. The current $I_p$ of the λ-sensor in the lean range is given by $$I_p = K_{O2}[O_2] + K_{NO}[NO] - K_{HC}[HC] \quad (I),$$

in which [$O_2$] or the measured concentration of oxygen or its vol % and in which the values for $K_{O2}$ in the equation (I) are or can be determined by calibration, since during calibration the sensor signals are measured with the concerned gas ingredients, i.e. when only $O_2$ or NO flows past the λ-sensor, or in the case of $K_{H2}$ in the equation (II) (see below) when only $H_2$+CO or HC+$CO_2$ flow by the λ-sensor.

When the CO, HC and NO relative amounts and $I_p$ are measured, $O_2$ can also be determined from the signal of the λ-sensor.

In the rich region downstream of the catalytic reactor 2 neither $O_2$ nor NO is present. $H_2$, CO and HC are the sensor relevant gases. The current signal $I_p$ of the λ-sensor is $$I_p = -K_{H2}[H_2] - K_{CO}[CO] - K_{HC}[HC] \quad (II).$$

The relative amount of $H_2$ can be determined knowing the Co and HC relative amounts present and $I_p$. Thus the λ-sensor can be used as an $H_2$ sensor.

Determination of the λ Value

In the lean range all required parameters are known so that λ values can be determined by the Brettschneider equation.

The Brettschneider equation (37) is taken from page 181 of the above-described 1974 article by Brettschneider for the present case of the lean exhaust gas of the form:

$$\lambda = \frac{[CO_2] + [O_2] + (H_{CV}/4 - O_{CV}/2)[CO_2] + [NO]/2}{(1 + H_{CV}/4 - O_{CV}/2)([CO_2] + [HC])}, \quad (III)$$

in which [$CO_2$] is the measured concentration of $CO_2$ in vol. % and $H_{cv}$ and $O_{cv}$ represent the hydrogen-hydrocarbon atomic ratio and the oxygen-hydrocarbon atomic ratio. Regarding the units see the above-named article of Brettschneider.

In the rich range the λ value is calculated in the following manner from the measured variables, wherein the mole fractions are represented by $\chi_{CO2}$, $\chi_{CO}$, $\chi_{HC}$ and $\chi_{H2}$.

Figure 4:
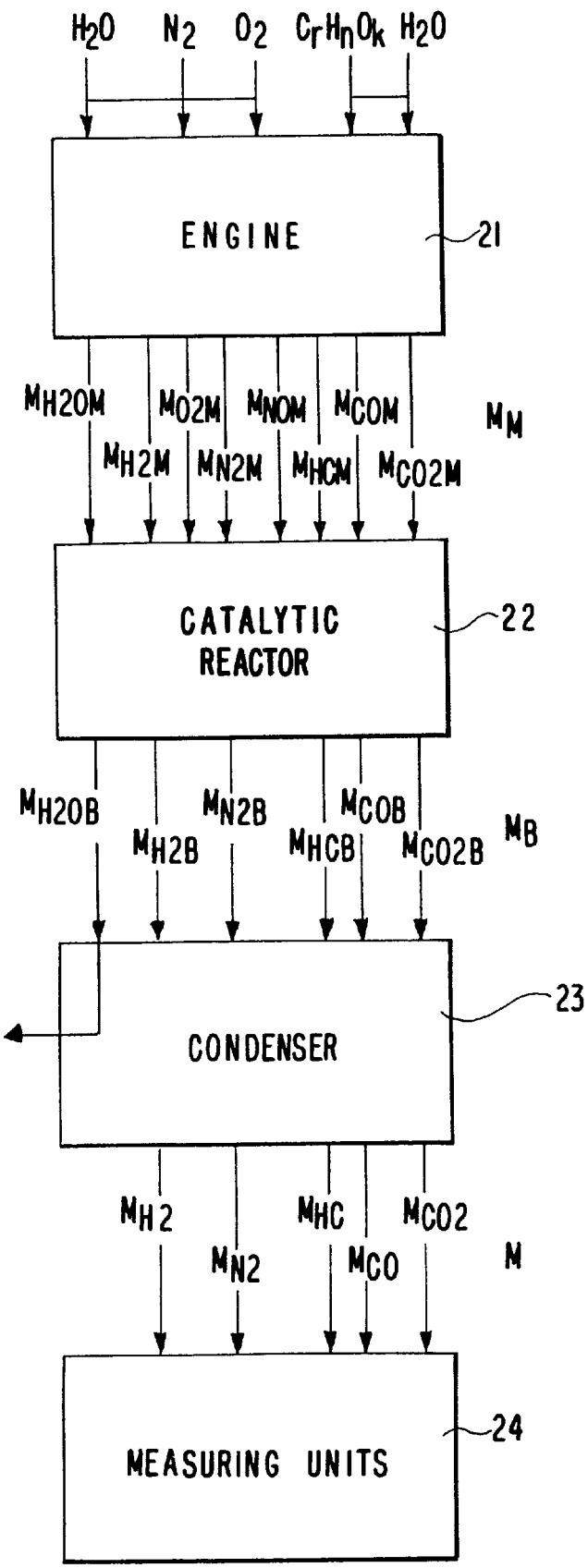
FIG. 4 is a schematic diagram illustrating the chemical transformations from the motor intake to the measurement apparatus inlet in the rich range.

The following assumptions are made regarding the input to the engine as shown in FIG. 4:

a) 1 mole of fuel $C_rH_nO_k$ that can contain w moles of water;

b) λ(r+n/4−k/2) moles of $O_2$;   (IV)

c) 3.76*λ(r+n/4−k/2) moles of $N_2$;

d) 4.76*f*λ(r+n/4−k/2) moles of $H_2O$, which can be supplied together with the $O_2$ and $N_2$ as water vapor. The variable f is the absolute humidity in relation to dry air. In FIG. 4 the engine including the catalytic converter is designated with the reference number 21, the heated catalytic reactor is designated with the reference number 22, the condenser, with 23 and the measurement apparatus for measuring the mole fractions $\chi_{CO2}$, $\chi_{CO}$, $\chi_{HC}$ and $\chi_{H2}$, with 24.

$m_{iM}$ represents the molar number at the output of the engine with the total molar number $M_M$, $m_{iB}$ represents the molar number at the output of the heated catalytic reactor with the total molar number $M_B$ and $m_i$ represents the molar number at the output of the condenser with the total molar number M (where i designates the ith chemical species). The mole fractions, $\chi_i = m_i/M$, were measured for CO, $CO_2$, $C_xH_yO_z$ (unburned hydrocarbons) and hydrogen. The following material balance relationships exist between the engine entrance and the output of the heated catalytic converter:

$$m_{CO2B} + m_{COB} + x^* m_{HCB} = m \quad (1) \text{ C Balance}$$

$$m_{N2B} + (\tfrac{1}{2})m_{NOB} = 3.76^*(r+n/4-k/2)\lambda \quad (2) \text{ N}_2 \text{ Balance}$$

$$m_{H2OB} + (y/2)m_{HCB} + m_{H2B} = n/2 + w + 4.76^* f (r+n/4-k/2)\lambda \quad (3) \text{ H}_2 \text{ Balance}$$

$$(\tfrac{1}{2})m_{COB} + m_{CO2B} + (\tfrac{1}{2})m_{H2OB} + (\tfrac{1}{2})m_{NOB} + (z/2)m_{HCB} = \lambda(r+n/4-k/2) + (w/2) + (1/2)^*4.76(r+n/4-k/2)f^*\lambda + (k/2) \quad (4) \text{ O}_2 \text{ Balance.}$$

The carbon material balance between the engine intake and the measuring apparatus inlet results in the following equation (5):

$$m_{CO2} + m_{CO} + x^* m_{HC} = m \quad (1) \text{ C Balance}$$

and at the measuring unit entrance $$\chi_i = m_i/M \quad (6).$$

The molar numbers for $H_2O$ can be calculated from the $H_2$ material balance and the $O_2$ material balance and can be set equal to each other, whereby the λ value as a function of the molar numbers of CO, $CO_2$, $C_xH_yO_z$ and $H_2$ downstream of the heated catalytic reactor can be determined.

From the $H_2$ material balance equation (3):

$$m_{H2OB} = n/2 - m_{H2B} - (y/2)m_{HCB} + w + 4.76^* f(r+n/4-k/2)\lambda \quad (7)$$

From the $O_2$ material balance equation (4):

$$m_{H2OB} = 2^*\lambda(r+n/4-k/2) - m_{COB} - 2m_{CO2B} - z^* m_{HCB} + k + w + 4.76(r+n/4-k/2)f^*\lambda \quad (8).$$

Since equation (7)=(8) and $m_{iB} = m_i$, $$\lambda = \frac{n-2k}{4(r+n/4-k/2)} + \frac{\{(1/2)m_{CO} + m_{CO2} + (1/4)(2z-y) - (1/2)m_{H2}\}}{(r+n/4-k/2)}. \quad (9)$$

The molar numbers of CO, $CO_2$, $C_xH_yO_z$ and $H_2$ downstream of the heated catalytic reactor are the same as the molar numbers downstream of the condenser. These molar numbers are known from $m_i = \chi_i M$. The M can be derived from a knowledge of m and the measurements of the mole fractions of CO, $CO_2$, $C_xH_yO_z$ and $H_2$.

From equations (5) and (6) the following equation (10) results:

$$M = \{m/(\chi_{CO} + \chi_{CO} + x^*\chi_{HC})\} \quad (10)$$

and equation (10) is substituted into equation (9) that results in the equation (11) for the λ value in the rich range:

$$\lambda = \frac{n-2k}{4(r+n/4-k/2)} + \frac{m\{(1/2)\chi_{CO} + \chi_{CO2} + (1/4)(2z-y) - (1/2)\chi_{H2}\}}{(r+n/4-k/2)(\chi_{CO2} + \chi_{CO} + x*\chi_{HC})} \quad (11)$$

In the following method for determining the λ value is now illustrated further with the aid of a numerical example, in which the fuel is burned with excess oxygen, whereby a rich fuel gas is produced.

EXAMPLE

A fuel has the empirical formula $CH_{1.817}$. It is burned in dry air in an automobile engine. The exhaust gas from the engine is conducted through a catalytic converter and subsequently guided through a heated catalytic reactor at for example a temperature of 600° C. in order to eliminate the $O_2$ and NO. The exhaust gas flows through the condenser, in which the water vapor condenses completely at a temperature of 0° C., after which it passes through the IR spectrometer and finally through the λ-sensor.

In the IR spectrometer the following values in vol. % were measured:

CO=2.665%

$CO_2$=14.158%.

$C_xH_y$=0.396% (evaluated as $CH_2$; the atomic ratio H:C in uncombusted hydrocarbon $C_xH_y$ is set at 2:1, since as experiment has shown it is somewhat greater than in the used fuel).

The λ-sensor has a current $I_p$ of −2,499 μA.

From equation (11) above the $H_2$ concentration is $$[H_2] = \{-I_p - K_{CO}[CO] - K_{HC}[HC]\}/K_{H2}$$

$$= (2,499 - 239 - 119)/383$$

$$= 5.590\%,$$

wherein $K_{H2}$=383 μA per % $H_2$, KCO=90 μA per % CO and $K_{HC}$=300 μA per % $C_{H2}$ were determined by calibration.

Thus because of equation (11) one obtains λ=0.812. If λ were to be calculated for the same experimental conditions however without $H_2$ measurement with CO=2.655 %, $CO_2$=14.158% and $CH_2$=0.396% according to Brettschneider, the value of λ that would result would be 0.908.

This large discrepancy causes the water gas equilibrium constant $K_p$ to deviate from 3.6 (as in the raw exhaust gas) in the exhaust gas downstream of the exhaust gas catalytic converter.

The disclosure in German Patent Application 198 04 985.4-52 of Feb. 7, 1998 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method and arrangement for analyzing exhaust gas from an internal combustion engine, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. An arrangement for analyzing exhaust gas from an internal combustion engine, said arrangement comprising
    a heated catalytic reactor (2, 22) connected to the internal combustion engine (21) to receive at least a portion of said exhaust gas from the internal combustion engine;
    a condenser (3, 23) connected to the heated catalytic reactor (2, 22) downstream of the catalytic reactor in the exhaust gas flow direction to receive said at least a portion of said exhaust gas from said catalytic reactor after said at least a portion of said exhaust gas passes through said catalytic reactor;
    an IR spectrometer (4) connected to the condenser (3, 23) downstream of the condenser in the exhaust gas flow direction to receive said at least a portion of said exhaust gas from said condenser after said at least a portion of said exhaust gas passes through said condenser; and
    a λ-sensor (5) connected downstream of the condenser so that said at least a portion of said exhaust gas passes by said λ-sensor after passing through said condenser.

2. The arrangement as defined in claim 1, wherein the condenser (3) is connected directly to said λ-sensor (5) upstream of said λ-sensor in the exhaust gas flow direction so that said at least a portion of said exhaust gas passes by said λ-sensor immediately after passing through said condenser.

3. The arrangement as defined in claim 1, wherein said λ-sensor (5) is connected to said IR spectrometer (4) downstream of said IR spectrometer in the exhaust gas flow direction so that said at least a portion of said exhaust gas passes by said λ-sensor (5) after passing through said IR spectrometer (4).

4. A method of analyzing exhaust gas from an internal combustion engine, said method comprising the steps of:
    a) reacting reducible exhaust gas components with oxidizable exhaust gas components in a heated catalytic reactor (2, 22) at temperatures greater than 450° C. to form a product mixture including water, $CO_2$, CO if present, hydrocarbons (HC), said product mixture including $H_2$ in a rich range or $O_2$+½ NO in a lean range;
    b) removing said water from the product mixture formed in step a);
    c) passing at least a portion of the product mixture by a λ-sensor (5) after removing said water in step b) to generate a λ-sensor signal ($I_p$);
    d) determining relative amounts of said $CO_2$, said CO if present and said hydrocarbons (HC) in said product mixture with an IR spectrometer (4) and from said λ-sensor signal ($I_p$); and
    e) determining relative amounts of said hydrogen or said $O_2$+½ NO from said λ-sensor signal ($I_p$) and said relative amounts of said $CO_2$, said CO if present, said hydrocarbons (HC) determined in step d).

5. The method as defined in claim 4, wherein in said lean range said relative amount of said $O_2$+½ NO is determined by means of said λ-sensor signal ($I_p$) that satisfies the following equation (I):

$$I_p=K_{O2}[O_2]+K_{NO}[NO]-K_{HC}[HC] \qquad (I),$$

wherein [$O_2$], [NO] and [HC] are the respective relative amounts of said $O_2$, NO and hydrocarbons expressed as concentrations and $K_{O2}$, $K_{NO}$ and $K_{HC}$ are constants, and by means of the relative amounts of said hydrocarbons and said $CO_2$ determined by said IR spectrometer (4).

6. The method as defined in claim 5, wherein said temperatures in said catalytic reactor (2) are from said 450° C. to 750° C.

7. The method as defined in claim 6, wherein said temperatures are about 600° C.

8. The method as defined in claim 4, wherein in said rich range said relative amount of said hydrogen is determined by means of said λ-sensor signal ($I_p$) using equation (II):

$$I_p = -K_{H2}[H_2] - K_{CO}[CO] - K_{HC}[HC] \quad (II),$$

wherein $[H_2]$, $[CO]$ and $[HC]$ are the respective relative amounts of said $H_2$, CO and hydrocarbons expressed as concentrations and $K_{H2}$, $K_{CO}$ and $K_{HC}$ are constants, and by means of the relative amounts of said hydrocarbons, said CO and said $CO_2$ determined by said IR spectrometer (4).

9. The method as defined in claim 8, wherein said temperatures in said catalytic reactor (2) are from said 450° C. to 750° C.

10. The method as defined in claim 9, wherein said temperatures are about 600° C.

11. The method as defined in claim 4, wherein said heated catalytic reactor (2, 22) is connected to the internal combustion engine (21) to receive said exhaust gas from the internal combustion engine; a condenser (3,23) is connected to the heated catalytic reactor (2, 22) downstream of the catalytic reactor (2,22) in the exhaust gas flow direction to receive said exhaust gas from said catalytic reactor after said exhaust gas has passed through said catalytic reactor and to remove said water from said exhaust gas; said IR spectrometer (4) is connected to the condenser (23) downstream of the condenser in the exhaust gas flow direction to receive said exhaust gas from said condenser after said exhaust gas has passed through said condenser and to said λ-sensor (5) by which at least a portion of the exhaust gas passes, either after passing said exhaust gas through said IR spectrometer or immediately after passing said exhaust gas through said condenser and before passing said exhaust gas through said IR spectrometer.

12. The method as defined in claim 11, further comprising calculating a λ value from said relative amounts of said exhaust gas components measured downstream of said condenser.

13. The method as defined in claim 12, wherein said λ value is determined in said lean range by means of a Brettschneider equation.

14. The method as defined in claim 12, wherein said λ value is determined in said rich range by means of a $H_2$ balance, a carbon balance, a $N_2$ balance and an $O_2$ balance between an engine intake and an output of the heated catalytic reactor and also the carbon balance between the engine intake and an entrance of the IR spectrometer or the λ-sensor.

* * * * *